United States Patent [19]

Van Rijn et al.

[11] Patent Number: 5,494,805
[45] Date of Patent: Feb. 27, 1996

[54] UNIT FOR THE DETECTION OF RESIDUES OF ANTIBACTERIAL COMPOUNDS IN LIQUIDS

[75] Inventors: Ferdinand T. Van Rijn, Delft; Robert Beukers, Nootdorp; Johannes Kerkhof, Rozenburg, all of Netherlands

[73] Assignee: Gist-Brocades N.V., Netherlands

[21] Appl. No.: 256,126

[22] PCT Filed: Feb. 9, 1994

[86] PCT No.: PCT/EP94/00356

§ 371 Date: Jun. 21, 1994

§ 102(e) Date: Jun. 21, 1994

[87] PCT Pub. No.: WO94/18343

PCT Pub. Date: Aug. 18, 1994

[30] Foreign Application Priority Data

Feb. 11, 1993 [EP] European Pat. Off. .............. 93200387

[51] Int. Cl.⁶ .......................... C12Q 1/18; C12Q 1/02; C12Q 1/14; C12N 1/20
[52] U.S. Cl. .................. 435/32; 435/29; 435/34; 435/4; 435/36; 435/253.6; 435/252.5; 435/253.4; 435/832
[58] Field of Search ............................ 435/32, 29, 4, 435/34, 832, 807, 32, 29, 34, 4, 36, 253.6, 252.5, 253.4, 832

[56] References Cited

U.S. PATENT DOCUMENTS

| | | | |
|---|---|---|---|
| 3,126,325 | 3/1964 | Poole et al. | 435/32 |
| 3,941,658 | 3/1976 | Lameris et al. | 435/32 |
| 4,219,621 | 8/1980 | Krenitsky | 435/32 |
| 4,601,985 | 7/1986 | Okonogi et al. | 435/32 |
| 4,929,546 | 5/1990 | Mayra-Makinen | 435/29 |
| 5,026,638 | 6/1991 | Saperstein | 435/32 |
| 5,094,955 | 3/1992 | Calandra et al. | 435/34 |
| 5,270,174 | 12/1993 | Rosenburg | 435/32 |
| 5,338,682 | 8/1994 | Sasaki et al. | 435/32 |
| 5,344,761 | 9/1994 | Citri | 435/32 |
| 5,354,663 | 10/1994 | Charm et al. | 435/32 |
| 5,380,648 | 1/1995 | Elango et al. | 435/32 |

FOREIGN PATENT DOCUMENTS

| | | |
|---|---|---|
| 0005891 | 12/1979 | European Pat. Off. . |
| 0285792 | 10/1988 | European Pat. Off. . |
| 0322591 | 5/1989 | European Pat. Off. . |
| 3613794 | 4/1986 | Germany . |

*Primary Examiner*—Douglas W. Robinson
*Assistant Examiner*—Louise N. Leary
*Attorney, Agent, or Firm*—Bierman and Muserlian

[57] ABSTRACT

The detection of residues of antibacterials such as antibiotics and sulpha compounds in liquids such as milk, water, meat juice, serum or urine is disclosed. A test unit comprises an agar medium inoculated with a suitable test organism and two or more redox indicators.

23 Claims, No Drawings

UNIT FOR THE DETECTION OF RESIDUES OF ANTIBACTERIAL COMPOUNDS IN LIQUIDS

The present invention relates to a method for the detection of residues of antibacterial compounds in liquids. The invention also relates to a unit for the detection of residues of antibacterial compounds in liquids and the use of the unit.

Similar tests have been described in GB-A-1467439, EP-A-0005891 and DE 3613794. These documents all deal with "ready to use" tests that make use of a test organism and will give a result generally between 2½ to 3½ hours by the change of colour of an acid-base or redox indicator added to the test system. The principle is that when an antibacterial compound is present in the sample liquid in a sufficient concentration to inhibit the growth of the test organism the colour of the indicator will stay the same, whilst when no inhibition occurs, the growth of the test organism is accompanied by the formation of acid or reduced metabolites that will change the colour of the indicator. In all these tests a single indicator is used to detect the formation of acid or reduced metabolites.

According to this invention a marked reduction in test duration, up to one hour, can be achieved when a combination of two or more indicators is used. Such a shortened test duration is of importance to the user because the quality of the sample liquid is known more quickly thus allowing an earlier delivery or processing etc.

Therefore the invention provides a method for detecting antibacterials in a test sample which comprises a) bringing a test organism and at least two redox indicators into an agar medium, b) allowing the test sample to come into contact with the agar medium such that antibacterials in the test sample inhibit the test organism in the agar medium.

The present invention also provides a unit for detecting antibacterials which comprises an agar medium comprising a test organism, optionally a separate nutrient source and two or more redox indicators which each can be present in the agar medium, in the test sample or in the separate nutrient source.

The unit of the present invention is useful for detecting residues of antibacterials such as sulpha compounds and antibiotics.

The unit may be used for detecting antibacterials in liquids, for example milk, water, meat juices, serum or urine.

The test organism is preferably a strain of Bacillus or Streptococcus. A preferred species of Streptococcus is *Streptococcus thermophilus*, more preferably *Streptococcus thermophilus* T101 (DSM 4022, deposited on Mar. 3, 1987). A strain of this species may be introduced into the agar medium, preferably in concentrations of $10^5$ to $10^9$ colony forming units (CFU) per ml agar medium.

A preferred species of Bacillus is *Bacillus stearothermophilus*, more preferably *Bacillus stearothermophilus* var. calidolactis C953. *Bacillus stearothermophilus* may be introduced into the agar medium preferably in concentrations of $10^5$ to $10^9$ CFU per ml of agar medium.

Examples of units useful for the purpose of the invention are transparent tubes, single or in a set or combined to a block of translucent material provided with a number of holes shaped therein.

A large variety of redox indicators may be used according to the process of the present invention. Such redox indicators are also known as redox mediators, redox catalysts and electron carriers. Examples of such compounds are Brilliant Black, Methylene Blue, Toluidine Blue, Safranine O, Indigo Carmin, Thionin, Gallocyanine, Nile Blue A, Brilliant Crocein MOO, Acid Yellow 38, Acid Orange 51, Acid Blue 120, Basic Blue 3, Azure A, Azure B, Congo Red, 1–10 Phenanthroline, Janus Green B, Brilliant Cresyl Blue. Other redox indicators (redox mediators, redox catalysts and electron carriers) may be used as well. Such compounds are commercially available see e.g. 'Stains, Dyes and Indicators', Catalogue of Aldrich Chemie. Preferably one of the indicators should give a colour change in the visible part of the spectrum. Preferred combinations are a) Brilliant Black and Methylene Blue b) Brilliant Black and Toluidine Blue and c) Brilliant Black and Nile Blue A.

Nutrients are added to enable the multiplication of the test organism.

The unit of the present invention optionally comprises at least part of the nutrients which are not incorporated in the agar medium and thus are added as a separate source, for example as a tablet or paper disc, which may be placed on the agar medium before carrying out the test. Nutrients may be present both in the agar medium and as a separate source. At least one of the redox indicators may be included in the separate nutrient source.

Nutrients and one or both redox indicators, e.g. in a tablet, may also be included in the units beforehand whereby measures are preferably taken to avoid moisture transport from the agar medium into the tablet. This may be done, e.g. by coating the tablet with a moisture-resistant layer, for example a wax, which coating must degrade or melt during the testprocedure. A wax having a melting temperature of 35° to 55° C., preferably 40° to 45° C., is suitable.

Strain C953 of *Bacillus stearothermophilus* var. calidolactis has been deposited with the Laboratory of Microbiology of the Technical University of Delft under the accession number LMD 74.1 in 1974 and with the Centraal Bureau voor Schimmelcultures (CBS), Baarn under the accession number CBS 760.83 in 1983 where the strain is available to the public. This microorganism is very sensitive to penicillins and other antibiotics and is a fast growing microorganism. It has the additional advantage that the optimal growing temperature is high (between 50°–70° C.). Only a few microbial species are able to grow at this temperature. There is therefore little possibility that organisms present in the test liquid or which have otherwise been included in the test system would affect the test result.

When the test organism is a Bacillus strain, it is preferably incorporated into the agar medium in the form of a spore suspension which may be prepared according to known methods (GB-A-1467439). The spore suspension is incorporated into the agar medium by known methods (GB-A-1467439).

According to a preferred embodiment of the present application the sensitivity of the test organism is adjustable. The sensitivity may be altered by various means, for example by adding certain substances, by changing the test conditions such as the pH or concentration of buffering substances, agar or spores or by varying ratio of the volumes in the volumes of agar and test liquid. Examples of substances that may be added are nucleosides, such as adenosine, or antifolates, such as trimethoprim, ormethoprim and tetroxoprim, which improve the sensitivity of the test organism to sulpha compounds, salts of oxalic acid or hydrofluoric acid which improve the sensitivity to tetracyclines, and cysteine to diminish the sensitivity to penicillins.

It is preferred to carry out the process of the present invention in such a way that the test organism stays alive but does not multiply in the agar medium. This is generally achieved by depriving the organism of nutrients until the test is carried out or/and by maintaining the culture at a sufficiently low temperature, for example below 30° C.

In the detection of residues of antibacterial compounds in fluids, preferably biological fluids, such as milk, water, meat juice, serum and urine, using the units as defined herein, a predetermined amount of the sample to be tested, for example 0.05 ml to 0.5 ml is placed on the agar medium (for example 0.2 ml to 3 ml), and the contents of the unit are incubated at or near the optimal temperature for the test organism for example 63° C. to 66° C. during a predetermined period, for example 60 to 120 minutes, after which the indicator colour is observed, indicating the presence or absence of antibacterials above a certain minimum concentration. The test is very simple to carry out, so that the person that performs the test does not have to be specially qualified. The test is completed in 1 to 2 hours after starting the test, which is markedly shorter than other microbial test systems where only one indicator is used.

All patent applications and patents mentioned in this application are herein incorporated by reference to the same extent as if each individual application or patent was specifically and individually indicated to be incorporated by reference.

The embodiments of the present application are illustrated by means of the following examples.

EXAMPLE I

Preparation of test tubes to detect antibiotics

A solution was made of 12 g agar and 9 g sodium chloride in 1000 ml distilled water. To this solution 2.5 ml of a 0.09M triethanolamine buffer solution (pH 8.0) was added. The final solution was sterilized for 20 minutes at 121° C. and cooled to about 60° C. To this sterile solution a sufficient amount of a suspension of *Bacillus stearothermophilus* var. calidolactis spores in distilled water was added to give a final concentration between $10^9$ and $10^{10}$ spores per liter and an amount of a sterile solution of Brilliant Black to give a final concentration of 80 mg per liter. Sterile tubes with a diameter of about 9 man were filled with 0.3 ml of the agar solution under aseptic conditions and immediately sealed e.g. with an aluminium foil. The contents of the test tubes was allowed to solidify while the tubes were held in an upright position. The thus prepared tubes were stored at a temperature between 5° C. and 15° C.

EXAMPLE II

Preparation of a test tube to detect antibiotics and sulpha compounds

The procedure described in Example I was followed except that together with the buffer solution an amount of a trimethoprim solution was added to give a final concentration of 60 µg per liter.

EXAMPLE III

Preparation of nutrient tablets

A mixture was made of 100 g dextrose, 160 g Avicel PH101, 50 g tryptose, 10 g phytone peptone, 15 g precirol and 500 mg of Toluidine Blue dissolved in 50 ml of ethyl alcohol. This mixture was sufficient to prepare 30000 tablets with a diameter of 3 mm and a thickness of 1.2 mm.

EXAMPLE IV

Carrying out a test

A test tube, prepared according to Example I or II, was opened by puncturing the seal and a nutrient tablet prepared according to Example III was added. Of the sample, e.g. a milk sample, to be investigated, 0.1 ml was added to the test tube and the test tube was placed in an incubator (waterbath or block heater) kept at 64° C. Observations were made after 1 hour and 20 minutes to 1 hour and 40 minutes.

If at this time the colour of the agar medium is yellow, the sample does not contain a detectable amount of an antibacterial compound (e.g. 0,003 I.U. or less of penicillin G or 0.1 µg or less of sulfamethazine per ml).

If, however, the colour of the agar medium is blue, the sample contains at least a detectable amount of an antibacterial compound (e.g. 0,006 I.U. or more of penicillin G or 0.2 µg or more of sulfamethazine per ml).

An in-between concentration, thus representing the just detectable amount may give a colour of the agar medium between yellow and blue.

EXAMPLE V

Comparison of the two indicator test unit with a single indicator test tube

Test tubes were prepared according to Example I or II. Nutrient tablets were prepared according to Example III. Similar nutrient tablets were prepared but without Toluidine Blue.

Tests were carried out according to Example IV with both types of nutrient tablets and an antibiotic-free milk sample. The test tubes in combination with the nutrients that do not contain Toluidine Blue took about one hour more to change colour, that is two hours 20 minutes to 2 hours 40 minutes, when compared with the combination test tube+nutrient tablet containing Toluidine Blue.

EXAMPLE VI

Preparation of variations and carrying out tests therewith

Test tubes were made according to Example I with the distinction that instead of a solution of Brilliant Black a solution was used containing a similar concentration of one of the following redox indicators: Brilliant Crocein MOO, Acid Yellow 38, Acid Yellow 51, Acid Blue 120 or Congo Red. Nutrient tablets were made according to Example II with the distinction that instead of Toluidine Blue a similar amount was used of one of the following redox indicators: Safranine O, Indigo Carmine, Thionin, Nile Blue A, Azure A, Azure B, Janus Green B, Brilliant Cresyl Blue ALD or Methylene Blue. The test was carried out according to Example IV with test tubes and nutrient tablets prepared according to the description given above.

A resulting change in colour indicates that the milk sample investigated does not contain detectable amounts of antibiotic and/or sulpha compounds. If the colour of the test does not change the milk sample does contain such residues. The test duration varied with the chosen combination of redox indicators but was markedly shorter than that of a one indicator test, in a similar way as described in Example V.

We claim:

1. A method for detecting antibacterials in a test sample which comprises a) bringing a test organism and at least two redox indicators into an agar medium, b) allowing the test sample to come into contact with the agar medium such that antibacterials in the test sample inhibit the test organism in the agar medium, and c) observing the contacted test sample for the presence or absence of a color change in the visible part of the spectrum which is indicative of the presence or absence of antibacterials.

2. The method according to claim 1 wherein the test organism is a strain of Bacillus or Streptococcus.

3. The method according to claim 1 where the test organism is a strain of *Bacillus stearothermophilus* var. calidolactis or a strain of *Streptococcus thermophilus*.

4. The method according to claim 1 wherein the agar medium is buffered.

5. The method according to claim 1 further comprising adding a nutrient source to the agar medium.

6. The method according to claim 5 wherein the nutrient source or part thereof is added in the form of a tablet or a paper disc.

7. The method according to claim 6 wherein the nutrient source further comprises at least one redox indicator.

8. The method according to any one of the preceding claims wherein the sensitivity of the test organism to antibacterial compounds is adjustable.

9. The method according to claim 1 which further comprises adding to the agar medium at least one substance which changes the sensitivity of the test organism to antibacterial compounds.

10. The method according to claim 9 wherein the substance which changes the sensitivity is an antifolate.

11. The method according to claim 10 wherein the substance which changes the sensitivity is trimethoprim, ormethoprim or tetroxoprim.

12. The method according to claim 1 wherein $10^5$ to $10^9$ colony forming units of test organism are present per milliliter agar medium.

13. A composition for detecting antibacterials which comprises an agar medium comprising a test organism, optionally a separate nutrient source and two or more redox indicators which each can be present in the agar medium or the separate nutrient source.

14. The composition according to claim 13 wherein the test organism is a strain of Bacillus or Streptococcus.

15. The composition according to claim 14 wherein the test organism is *Bacillus stearothermophilus* or *Streptococcus thermophilus*.

16. The composition according to claim 13 wherein the agar medium is buffered.

17. The composition according to claim 13 wherein the agar medium further comprises at least one nutrient.

18. The composition according to claim 13 wherein the separate nutrient source comprises at least one redox indicator.

19. The composition according to claim 13 wherein the separate nutrient source is in the form of a tablet or paper disc.

20. The composition according to claim 13 wherein the sensitivity of the test organism is adjustable.

21. The composition according to claim 13 which further comprises at least one substance which changes the sensitivity of the test organism to antibacterial compounds.

22. The composition according to claim 21 wherein the substance which changes the sensitivity of the test organism is an antifolate.

23. The composition according to claim 22 wherein the substance which changes the sensitivity of the test organism is trimethoprim or tetroxoprim.

* * * * *